United States Patent [19]

Häkkinen

[11] 4,267,832
[45] May 19, 1981

[54] EXPIRATION VALVE APPARATUS FOR USE WITH A RESPIRATOR OR LIKE APPARATUS

[76] Inventor: Taisto Häkkinen, Kaarlonkatu 25, 13210 Hämeenlinna 21, Finland

[21] Appl. No.: 30,844

[22] Filed: Apr. 17, 1979

[30] Foreign Application Priority Data

Apr. 18, 1978 [FI] Finland ................................. 781171

[51] Int. Cl.³ ............................................ A61M 16/00
[52] U.S. Cl. .......................... 128/205.24; 128/207.16; 137/102; 137/DIG. 9
[58] Field of Search ...................... 128/205.24, 204.26, 128/205.11, 204.29, 205.13, 204.18, 205.17, 204.24, 207.12; 137/DIG. 9, 102

[56] References Cited

U.S. PATENT DOCUMENTS

| 3,097,642 | 7/1963 | Russell | 128/205.24 X |
| 3,688,794 | 9/1972 | Bind et al. | 128/205.24 X |

FOREIGN PATENT DOCUMENTS

| 798660 | 11/1968 | Canada | 128/205.24 |
| 627416 | 3/1936 | Fed. Rep. of Germany | 137/DIG. 9 |

*Primary Examiner*—Henry J. Recla
*Attorney, Agent, or Firm*—Steinberg & Raskin

[57] ABSTRACT

Valve apparatus for use in connection with a respirator or like apparatus, suitable for use in resuscitation, the valve apparatus providing a stepless or continuous adjustment of the counter-pressure presented to expiration by the patient. The apparatus includes a rear portion having an opening formed therein which provides a fluid inlet into the interior space of the rear portion for an inhalation, such as air or oxygen and atomized drugs from a respirator or the like, a diaphragm valve member associated with the rear portion which opens to allow the passage of the inhalation from within the rear member but which closes during expiration to prevent the passage of exhalation into the interior of the rear member, a front portion associated with the rear portion in a manner such that the diaphragm valve member is interposed between the interior spaces of the front and rear portions, the front portion having an aperture which provides fluid communication between the interior of the front portion and the external atmosphere and an adjustment ring mounted around the first portion for rotation with respect thereto, the adjustment ring having an aperture formed therein adapted to be moved into overlapping relationship with the aperture formed in the first portion to change the effective size of the front portion aperture. In this manner, a stepless or continuous adjustment of the counter-pressure presented to expiration is achieved.

5 Claims, 5 Drawing Figures

U.S. Patent    May 19, 1981    4,267,832
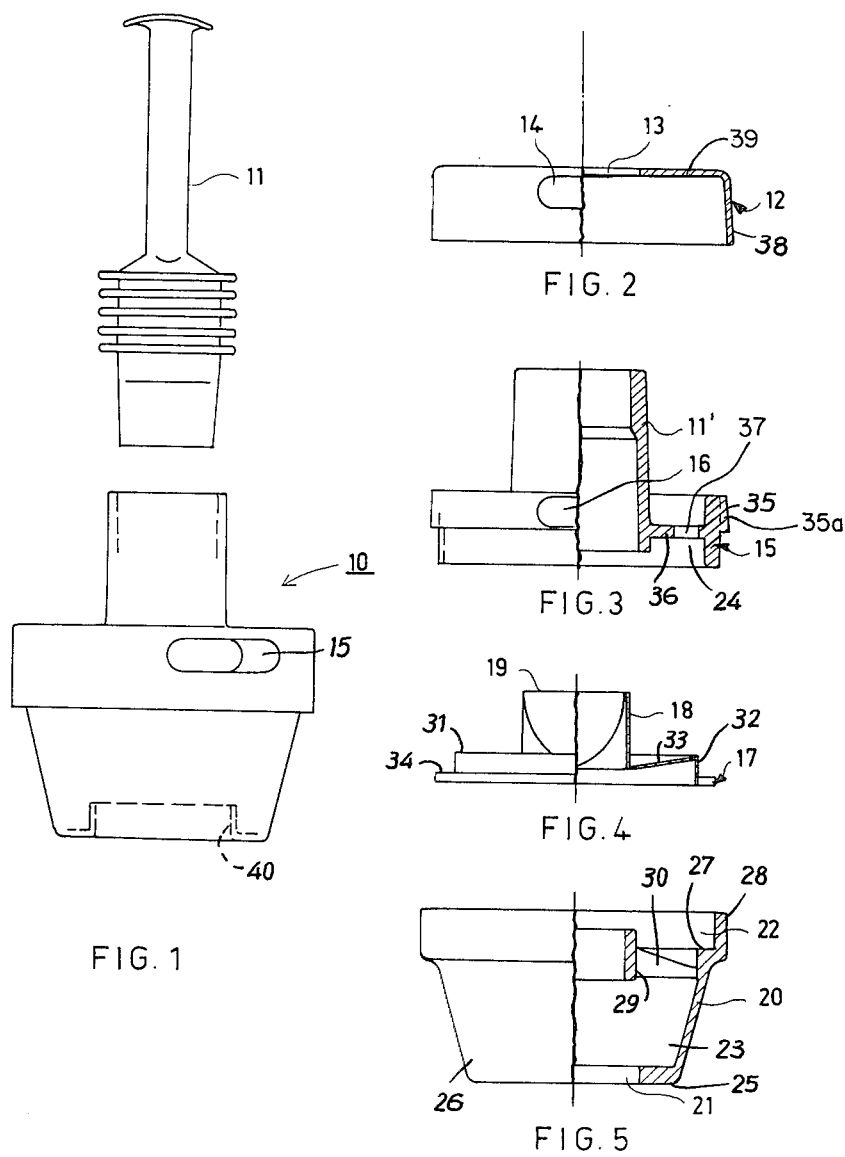

4,267,832

EXPIRATION VALVE APPARATUS FOR USE WITH A RESPIRATOR OR LIKE APPARATUS

BACKGROUND OF THE INVENTION

This invention relates generally to valves for use in connection with respirators or like apparatus suitable for use in resuscitation and, more particularly, to a valve apparatus for use in connection with such apparatus for providing a stepless or continuous adjustment of the counter-pressure presented to expiration by the patient.

It is often advisable or necessary in connection with providing respiration by means of a respirator or like apparatus to be able to adjust the counter-pressure which is presented to the expiration of exhalation of the patient. In this connection, it is highly desirable to be able to adjust the extent of the counter-pressure presented during respiration in a stepless or continuous manner so that the most advantageous counter-pressure may be utilized under the particular circumstances.

In the present applicant's Finnish patent application No. 753,748, a respirator apparatus is disclosed which is provided with an expiration valve and wherein the counter-pressure to expiration by the patient is adjustable in a stepless or continuous manner. In this design, the expiration valve is located directly over the drug atomizer. The expiration valve includes a sleeve which is located between the mouthpiece of the respirator and the drug atomizer in which a flap, located at the end of the sleeve distal from the mouthpiece, is adapted to open on inspiration and close on expiration.

An aperture is formed in the sleeve which leads to the expiration valve. The sleeve is adapted to be rotated to achieve a stepless adjustment of the counter-pressure presented during expiration.

The expiration valve disclosed in the above-identified patent application further includes a diaphragm which functions to inhibit the outward flow through the exit aperture of the expiration valve during inspiration but which allows the inhalant, such as air or oxygen and atomized drugs, to pass from the exit ports or apertures at exhalation.

The design of the expiration valve described above is, however, not entirely satisfactory. More particularly, the expiration valve described above has a relatively complex construction which is necessarily costly in manufacture. Moreover, the location of the expiration valve directly over the drug atomizer seriously restricts the use thereof in connection with certain respirators. Thus, where respirators are assembled of standard components constituting a type of modular system, it is not always possible to utilize the expiration valve described above in association therewith. Still further, the placement of the expiration valve over or on top of the drug atomizer also restricts the various options normally available in connection with the assembly and modification of the respirator.

SUMMARY OF THE INVENTION

Accordingly, one object of the present invention is to provide a new and improved valve apparatus for use in connection with a respirator or like apparatus, suitable for use in resuscitation, which provides a stepless or continuous adjustment of the counter-pressure presented to expiration by the patient during respiration.

Another object of the present invention is to provide such a new and improved expiration valve apparatus which is extremely simple in construction and therefore inexpensive in manufacture.

A still further object of the present invention is to provide such a new and improved expiration valve apparatus which may be utilized in association with various types of respirators and which does not limit the possibilities and options of modifying the structure of the respirator in view of the particular circumstances.

Briefly, in accordance with the present invention, these and other objects are attained by providing an expiration valve including a rear portion having at least one wall which defines an interior space therewithin, the wall having an opening formed therein which is adapted to provide a fluid inlet into the interior space of the rear portion for an inhalation, such as air or oxygen and an atomized drug, from a drug atomizer of a respirator or like apparatus suitable for resuscitation use. A one-way valve means is operatively associated with the rear portion and is adapted to open to allow the passage of the inhalation from the interior space of the rear member through the valve means under the effect of the incoming pressure flow during inspiration by the patient and for closing during expiration by the patient when the incoming pressure flow ceases so that passage of exhalation into the rear member interior space is prevented. A front portion having an interior space defining wall is operatively associated with the rear portion in a manner such that the one-way valve means is interposed between the interior spaces of the front and rear portions. The front portion has an aperture formed in the wall which provides fluid communication between the interior space within the front portion and the external atmosphere. An adjustment member is moveably mounted on the front portion, the adjustment member being adjustably or selectively movable over the aperture formed in the front portion in a continuous, stepless manner so that the relative position of the adjustment member over the front portion aperture will determine the effective size of the aperture which can vary from a fully open to a fully closed extent.

The front and rear portions together with the one-way valve means are constructed in a manner such that a fluid passage is defined therethrough for the inhalation such that the path of flow of the inhalation is prevented from communicating with the aperture formed in the front portion during inspiration by the patient. During expiration, the exhalation is prevented from entering the interior of the rear portion by the closed valve means whereupon the exhalation is directed to the aperture in the front portion which determines the counter-pressure to such expiration.

Preferably, the adjustment member comprises an adjustment ring mounted around the front portion for rotation with respect thereto. An aperture is formed in the adjustment ring which can be located through suitable rotation of the adjustment ring with respect to the front portion in a manner such that it overlaps the front portion aperture to a desired degree to determine the effective size of the front portion aperture. The one-way valve means preferably comprises a diaphragm valve member having a diaphragm component adapted to open under the effect of the incoming pressure flow during inspiration and to close during expiration, when the incoming pressure flow has terminated.

DESCRIPTION OF THE DRAWINGS

A more complete appreciation of the invention and many of the attendant advantages thereof will be readily appreciated as the same becomes better understood by reference to the following detailed description when considered in connection with the accompanying drawings in which:

FIG. 1 is a front elevational view of the expiration valve apparatus according to the present invention and further illustrating the mouth piece of a respirator just prior to connection of the latter to the former;

FIG. 2 is a front elevation view in partial section of a preferred adjustment member, namely an adjustment ring, which comprises a component of the expiration valve illustrated in FIG. 1;

FIG. 3 is a front elevation view in partial section of the front portion of the expiration valve illustrated in FIG. 1;

FIG. 4 is a front elevation view in partial section of a preferred embodiment of the one-way valve means, namely a diaphragm valve member, comprising a component of the expiration valve apparatus of the present invention; and FIG. 5 is a front elevation view in partial section of the rear portion of the expiration valve apparatus illustrated in FIG. 1.

DESCRIPTION OF THE PREFERRED EMBODIMENTS

Referring now to the drawings, wherein like reference characters designate identical or corresponding parts throughout the several views, the expiration valve according to the present invention is generally designated 10. FIG. 1 illustrates the expiration valve 10 in assembled form and FIGS. 2-5 each illustrate one of the components which make up the expiration valve 10. Although the preferred embodiment illustrates the expiration valve 10 as being formed of a plurality of separately formed components, it is understood that within the scope of the claims, two or more of these components may be integrally formed with each other.

Generally, the expiration valve 10 of the present invention includes a rear portion 20 (FIG. 5) defining an interior space 23, and a one-way valve member 17 (FIG. 4) adapted to be operatively associated with the rear portion 20 in a manner described below. The one-way valve member 17 functions to allow the passage of inhalation from the interior space 23 of rear portion 20 therethrough under the effect of incoming pressure flow during inspiration and for closing during expiration when the incoming pressure flow ceases to prevent the passage of exhalation into the rear portion interior space 23. A front portion 15 defining an interior space 24 is also operatively associated with the rear portion 20 in a manner such that the one-way valve member 17 is interposed between the interior spaces 23, 24 of the rear and front portions 20, 15. Front portion 15 (FIG. 3) has an aperture or exhalation port 16 formed in the wall which defines the front portion so as to provide fluid communication between the front portion interior space 24 and the external atmosphere, as described in greater detail below. Finally, an adjustment member which, in the present embodiment, takes the form of an adjustment ring 12, is rotatably mounted over the front portion 15 as best seen in FIG. 1. The adjustment ring 12 has an aperture 14 provided therein which is movable over the front portion through rotation of adjustment ring 12 so that the aperture 14 can be located in overlapping relationship to the aperture of exhalation port 16 formed in front portion 15, the extent of such overlapping being selectively adjustable in a stepless or continuous manner. Thus, the effective size of the exhalation port 16 may be selectively steplessly varied from a fully open to a fully closed configuration depending upon the position of the adjustment ring 12 with respect to front portion 15. In this manner, the valve apparatus provides a stepless or continuous adjustment of the counter-pressure presented to expiration.

Referring to FIG. 5 wherein the rear portion 20 comprising a component of the expiration valve 10 is illustrated, rear portion 20 comprises a bowl shaped member having a bottom wall 25 and a circumferentially extending side wall 26 which extends upwardly and outwardly. A horizontal, annularly extending shoulder 27 is provided at the upper region of side wall 26 while a circumferentially extending flange extends vertically from the outer edge regions of shoulder 27. A cylindrical collar portion 29 is centrally located within interior space 23 and is coaxial with the central axis of rear portion 20. Collar portion 29 is located within space 23 by a plurality of radially extending ribs 30 each of whose ends are connected to collar portion 29 and side wall 26. An aperture 21 is formed in the bottom wall 25 of rear portion 20 which is adapted to provide a fluid inlet into the interior space 23 thereof for an inhalation from a drug atomizer of a respirator or the like over which the expiration valve 10 is located.

The one-way valve member 17 comprises, in the preferred embodiment of the present invention a diaphragm valve member. More particularly, the diaphragm valve member 17 is formed by a dish shaped body portion 31 defined by a circularly extending vertical wall 32 and a downwardly and inwardly extending transverse wall 33 which intersects at its inner edge region the lower edge of an upwardly extending cylindrical diaphragm component 18. Diaphragm component 18 comprises a wedge-shaped diaphragm whose apex is designated 19. A circumferentially extending flange 34 horizontally extends from the lower edge of the vertical wall 32 of body portion 31. The outer diameter of flange 34 is such that upon the diaphragm valve member 17 being located within the space 22 defined by flange 28 of rear portion 20, the lower surface of flange 17 will rest upon the annular shoulder 27 of rear portion 20 and so that the collar portion 29 in rear portion 20 communicates with the cylindrical diaphragm component 18.

The diaphragm valve member 17 is thus adapted to open under the effect of the inhalation admitted into the interior 23 of rear portion 20 through aperture 21 during inspiration by the patient as described below. However, the diaphragm valve member 17 will close during expiration when the pressure flow from the drug atomizer of the respirator has terminated, also described below.

Referring now to FIG. 3, the front portion 15 comprising a component of the present invention is illustrated and includes a circumferentially extending substantially cylindrical outer side wall or skirt 35 having an upper portion 35a of increased radial dimension. A substantially cylindrical connector portion 11' is integrally formed with side wall 35 by means of a transverse web 36, the connector portion 11' being coaxial with side wall 35. A plurality of openings 37 (only one shown) are formed in web 36 for reasons which will become clear hereinbelow.

Front portion 15 is operatively associated with rear portion 20 by locating the same within the space 22 defined by flange 28 of rear portion 20. The diameter of side wall 35 of front portion 15 is such that the lower edge surface of side wall 35 abuts against the upper surface of flange 34 of diaphragm valve member 17, which itself rests upon the annular shoulder 27 as described above. Upon locating the front portion 15 as described above, the cylindrical diaphragm component 18 is received within the connector portion 22'. It is also noted that the laterally extending shoulder defined by the side wall portion 35a of increased thickness will abut against the upper edge surface of flange 28 of rear portion 20.

An aperture or exhalation port 16 is provided in and extends through the enlarged side wall portion 35a of front portion 15. Exhalation port 16 has an elongated or oblong shape, it being understood that only approximately one half of the exhalation port 16 is shown in FIG. 3 due to the particular sectional view presented therein.

Turning now to the adjustment ring 12 illustrated in FIG. 2, this component of the expiration valve comprises a member having an inverted cup-shaped configuration defined by a substantially cylindrical circumferentially extending side wall 38 and a transverse top wall as skirt 39. A circular aperture 13 is centrally formed in top wall 39 so that adjustment ring 12 may be located over front portion 15, aperture 13 receiving the connector portion 11', in a manner such that the inner surface of side wall 38 is contiguous with the outer surface of enlarged side wall portion 35a of front portion 15. It is readily apparent that from such construction, adjustment ring 12 may be selectively rotated around front portion 15.

An aperture 14 having a configuration similar to that of exhalation port 16 is formed in the skirt or side wall 38 of adjustment ring 12. As best seen in FIG. 1, the skirt or side wall 38 of adjustment ring 12 overlaps over the outer surfaces of enlarged side wall portion 35a of the skirt 35 or front portion 15 as well as the outer surface of flange 28 of rear portion 20.

In operation, the expiration valve 10, assembled in the manner described above, is located over the drug atomizer of a respirator (not shown) in a manner such that the respiration air or oxygen and atomized drugs, if any, are introduced into the interior space 23 of rear portion 20 through aperture 21 as schematically shown at 40 in FIG. 1. During the patient's inspiration, the inhalation received within interior space 23 which is at a pressure greater than ambient causes the diaphragm component 18 of diaphragm valve member 17 to open whereby the inhalant flow through the connector portion 11' of front portion 15 into the mouth piece 11 (FIG. 1) above the respirator and, of course, from where it flows into the patient's lungs. In this connection, it is noted that by virtue of the cylindrical diaphragm component 18 extending within the connector portion 11' in the manner described above, the path of flow of the inhalation is substantially prevented from communicating with the exhalation port 16 during inspiration.

During expiration by the patient, the pressurized flow of inhalation from the drug atomizer terminates so that the diaphragm component 18 of diaphragm valve member 17 closes. Thus, the flow of the patient's exhalant is transmitted through the respirator mouth piece 11 and the connector portion 11' of front portion 15 whereupon it enters the interior space 24 of front portion 15.

The exhalation thus is directed through openings 37 formed in web 36 into the region above web 36. Of course, the exhalation is prevented from leaving front portion 15 through the upper regions thereof by virtue of the top wall 39 which overlies and essentially seals the same. Accordingly, the exhalation exits from the expiration valve 10 through the exhalation port 16 formed in front portion 15.

According to the present invention, the effective size of the exhalation port 16 can be varied in a stepless or continuous manner by the suitable rotational positioning of adjustment ring 12 so that the aperture 14 formed therein overlaps exhalation port 16 to a desired extent. It is thus apparent that it is possible by suitably rotating adjustment ring 12 to adjust in a stepless or continuous manner the counter-pressure presented by the expiration valve 10 to the flow of exhalant. More particularly, as adjustment ring 12 is rotated the mutual relative positioning of the aperture 14 of adjustment ring 12 with respect to exhalation port 16 formed in front portion 15 will change whereby the counter-pressure to expiration will correspondingly change. Of course, when aperture 14 of adjustment ring 12 is in precise registration with exhalation port 16, the counter-pressure presented by the expiration valve 10 to the patient's expiration is at a minimum. Similarly, when the adjustment ring has been rotated in a manner such that the side wall 38 thereof completely covers exhalation port 16, the counter-pressure to expiration is at a maximum.

The expiration valve according to the present invention is suitable for use not only in connection with respirators but, in addition, is also amenable to use with other kinds of resuscitation apparatus such, for example, as spherical resuscitation apparatus, etc. Further, the expiration valve of the present invention is suitable for use with respirators of modified configuration as well as respirators which are assembled of standard components which constitute a modular system as will be understood by one having ordinary skill in the art.

Obviously, numerous modifications and variations of the present invention are possible in the light of the above teachings. For example, it is possible to utilize other types of one-way valve structures in lieu of the diaphragm valve described above in connection with the preferred embodiment of the invention. It is also possible to utilize other configurations for the adjustment member which, in the presently disclosed embodiment, constitutes adjustment ring 12. For example, an arcuate leaf member may be slidably located over the outer surface of side wall portion 35a which may be steplessly or continuously moved over exhalation port 16 to change the effective opening thereof. It is therefore to be understood that within the scope of the appended claims, the invention may be practiced otherwise then as specifically disclosed herein.

What is claimed is:

1. Valve apparatus for use in connection with a respirator or like apparatus suitable for use in resuscitation for permitting both inhalation and exhalation, the valve apparatus adapted to provide stepless or continuous adjustment of the counter-pressure presented to expiration, comprising:

a rear portion having at least one wall defining an interior space therewithin, said wall having an opening formed therein adapted to provide a fluid inlet into said interior space and including means adapted to be connected to a drug atomizer of a respirator or like apparatus suitable for resuscitation use to receive inhalation gas therefrom;

one-way diaphragm valve means operatively associated with said rear portion adapted to open upon inhalation to allow the passage of the inhalation from said rear portion interior space therethrough under the effect of incoming pressure flow during inspiration and being adapted to close during expiration when the incoming pressure flow ceases to prevent the passage of exhalation into said rear portion interior space;

a front portion having at least one wall defining an interior space therewithin, said one wall including tubular means for connecting the same to a mouthpiece of the respirator or the like and a substantially cylindrical skirt portion, concentrically disposed with respect to said tubular means said front portion being operatively connected to said rear portion in a manner such that said one-way valve means is interposed between the interior spaces defined by said front and rear portions, said substantially cylindrical skirt portion having an aperture formed therein providing communication between said front portion interior space and the external atmosphere, said one wall of said front portion including means associated with said one-way diaphragm valve means to prevent flow through said aperture during inhalation and permit flow through said tubular means, said interior space of said front portion and said aperture during exhalation; and an adjustment ring including a substantially cylindrical skirt portion having an aperture formed therethrough, said ring being concentrically and rotatably mounted about said tubular means on said front portion with said ring skirt portion being concentric with and overlapping said front portion skirt portion, said ring being rotatable with respect to said front portion in a continuous and stepless manner such that the adjustment ring aperture is adapted to be moved into overlapping relationship with respect to said front portion aperture to any desired degree so that the effective size of said front portion aperture can be steplessly and continuously varied.

2. Valve apparatus as recited in claim 1 wherein said rear portion includes an inwardly directed annularly extending shoulder and a substantially central collar portion surrounded by and coaxial with said shoulder defining the path of flow of the inhalation and wherein said one-way diaphragm valve means includes a diaphragm valve member having a cylindrical component comprising a wedge-shaped diaphragm extending into said tubular means flange and a component extending circumferentially of said cylindrical component, said flange component of said diaphragm member having an outer peripheral edge supported on said shoulder of said rear portion, said front portion has a substantially central connector portion extending from said tubular means and being in substantial alignment with said collar portion and spaced therefrom, said flange component having an inner annular portion disposed between said collar portion and said connector portion whereby, said central collar portion, cylindrical diaphragm component and central connector portion effectively prevents inhalation gas flow from communicating with said front portion aperture during inspiration.

3. Valve apparatus as recited in claim 2 wherein a fluid flow passage is defined between said central connector portion and cylindrical diaphragm component which communicates with said front portion aperture so that the exhalation will be directed to said front portion aperture during expiration.

4. Valve apparatus as recited in claim 1 wherein said tubular means comprises a connector cone portion adapted to be connected to the mouth piece of the respirator or like apparatus.

5. Valve apparatus as recited in claim 1 wherein said one-way valve means comprises a diaphragm member including a wedge-shaped diaphragm component having an apex adapted to open and close during inspiration and expiration, respectively.

* * * * *